United States Patent [19]

Temler

[11] Patent Number: 4,993,273
[45] Date of Patent: Feb. 19, 1991

[54] WOOD CHIP SAMPLING APPARATUS

[75] Inventor: Jan S. Temler, Spanish Fort, Ala.

[73] Assignee: International Paper Company, Purchase, N.Y.

[21] Appl. No.: 420,073

[22] Filed: Oct. 11, 1989

[51] Int. Cl.⁵ .............................................. G01N 1/20
[52] U.S. Cl. ................................ 73/864.32; 73/863.54
[58] Field of Search ..................... 73/864.32, 863.54; 162/49, 198, 263

[56] References Cited

U.S. PATENT DOCUMENTS

| 2,937,529 | 5/1960 | Laprise | 73/863.52 |
| 4,024,765 | 5/1977 | Aonnenc | 73/863.83 |
| 4,026,155 | 5/1977 | Joseph | 73/863.55 |
| 4,056,983 | 11/1977 | Mazzetti | 73/863.57 X |
| 4,107,599 | 8/1978 | Preikschet | 324/689 |
| 4,391,359 | 7/1983 | Lapointe | 192/23 |
| 4,558,602 | 12/1985 | Redding | 73/864.32 X |
| 4,918,999 | 4/1990 | Wansheu et al. | 73/863.54 |

FOREIGN PATENT DOCUMENTS

| 726466 | 4/1980 | U.S.S.R. | 73/864.32 |
| 890123 | 12/1981 | U.S.S.R. | 73/863.54 |
| 1010501 | 4/1983 | U.S.S.R. | 73/863.54 |

Primary Examiner—Tom Noland
Attorney, Agent, or Firm—Walt Thomas Zielinski

[57] ABSTRACT

A wood chip sampling apparatus which includes a chip collecting tray. The tray moves to a first location where it collects a sample of downwardly flowing wood chips and then to a second location where it discharges the chips into a chip sample bin for later analysis. The tray is pivoted about a horizontal axis and is weighted on one side of the pivot axis so that it automatically assumes a horizontal, chip receiving orientation after chip discharge. An abutment prevents the tray from pivoting and dumping collected chips in the first tray location, the tray automatically pivotting to dump the chips when in the second location. The collecting tray thus reciprocates along a horizontal path and pivots over a range of 90 degrees.

8 Claims, 3 Drawing Sheets 4,993,273

WOOD CHIP SAMPLING APPARATUS

BACKGROUND OF THE INVENTION

This invention relates to the art of wood chip sampling. In the papermaking art, it is often desired to determine the quality, size, composition, etc. of wood chips. Typically, wood chips are sorted by size or by weight, with those sizes or weights selected for particular parts of the papermaking process being sampled from time to time. A sample collecting receptacle is intermittently or periodically placed in the stream or flow of the wood chips, filled, withdrawn from the stream and then the wood chip sample is transferred to an analyzing station/apparatus for determination of its qualities or properties.

A typical wood chip sampling machine is described in U.S. Pat. No. 2,937,529 issued to Laprise. In the Laprise apparatus, a wood chip collecting tray is carried by a frame member 17, 20 which reciprocates along an axis in a horizontal plane. The reciprocation is into a stream of falling wood chips which are to be analyzed, and out of the stream. When pulled back out of the stream, the tray of Laprise automatically pivots to a substantially vertical position to thereby discharge or dump the collected wood chips into a chip analysis collection chamber. In order to assume a horizontal position for the next chip collecting cycle, an abutment 10 is required to tilt the vertically disposed sample collecting tray to once more assume a horizontal position. Further, with each cycle the tray turns 180 degrees, so that after two cycles the tray has turned 360 degrees and keeps on turning, in a counterclockwise motion, throughout the sample collecting operation. Laprise thus finds it necessary to provide a sample collection tray which has two operational or chip receiving surfaces, on account of the required rotation of the tray caused by continuing striking of abutment 10.

SUMMARY OF THE INVENTION

According to the practice of this invention, a wood chip sampling apparatus is provided with a sample collecting tray, the tray being weighted and cooperating with abutments in such a manner that it automatically assumes a horizontal position after chip dumping and will assume a vertical or dumping position only when disposed over a wood chip sample collecting chamber, due to the weight of wood chips therein. The tray is carried by a frame, the frame and tray reciprocating between a chip collecting location and a chip dumping location. The tray of this invention pivots over a range of 90 degrees during its operation, as opposed to the Laprise construction wherein the sample collecting tray continually pivots in a series of full or 360 degrees rotations.

By the construction of this invention, an abutment is not required to rotate the tray to its horizontal, chip collecting position. The construction is such that certain abutments employed are not subject to a direct colliding type action, as is the case with the Laprise construction. In one embodiment of the invention the tray pivots about an axis parallel to the direction of tray reciprocation, while in another embodiment the tray pivots about an axis perpendicular to the direction of tray reciprocation.

DESCRIPTION OF THE INVENTION

Figure 1:
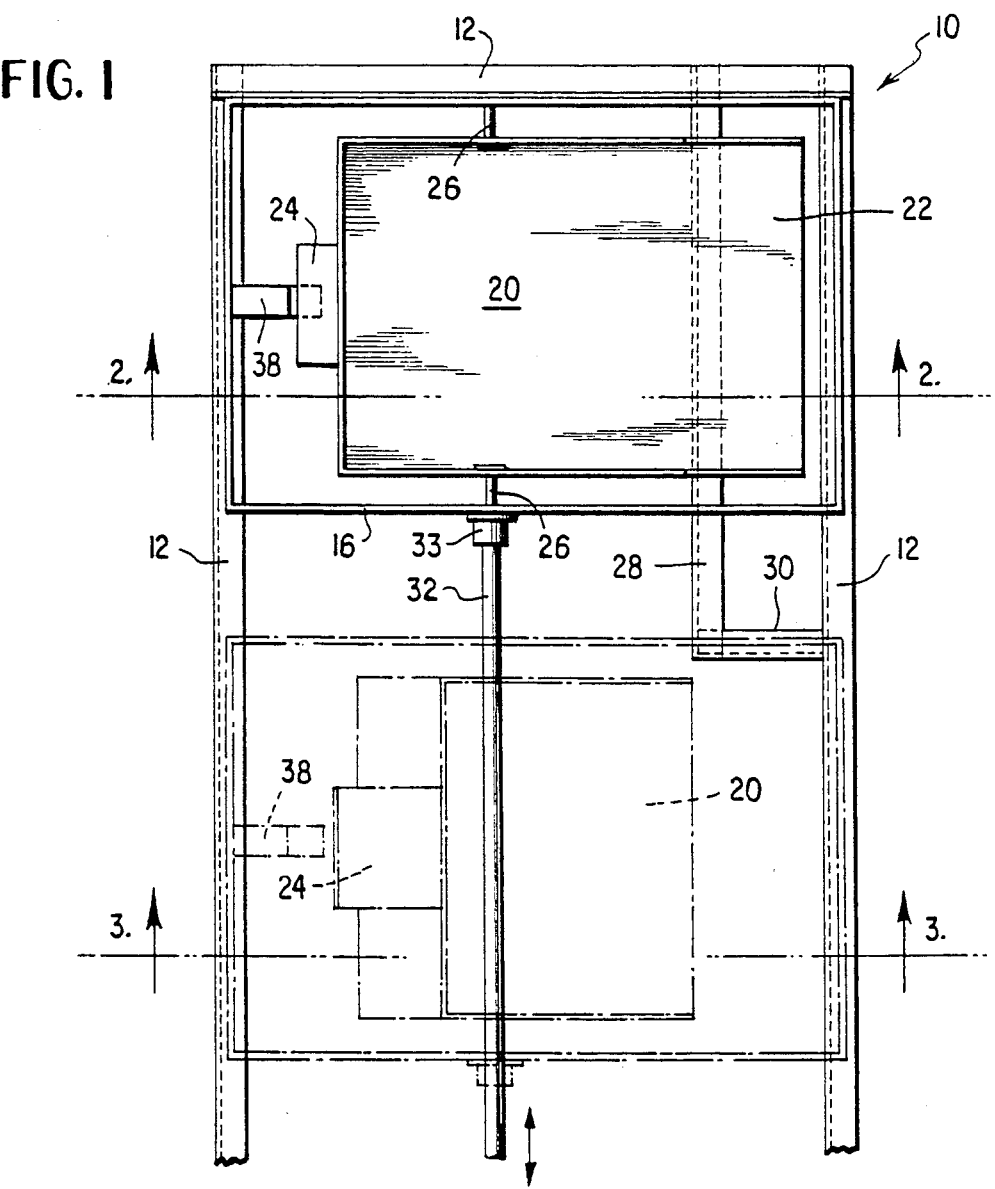
FIG. 1 is a plan view of a wood chip sample apparatus including a collecting tray and associated frame portions, according to a first embodiment of the invention.
Figure 2:
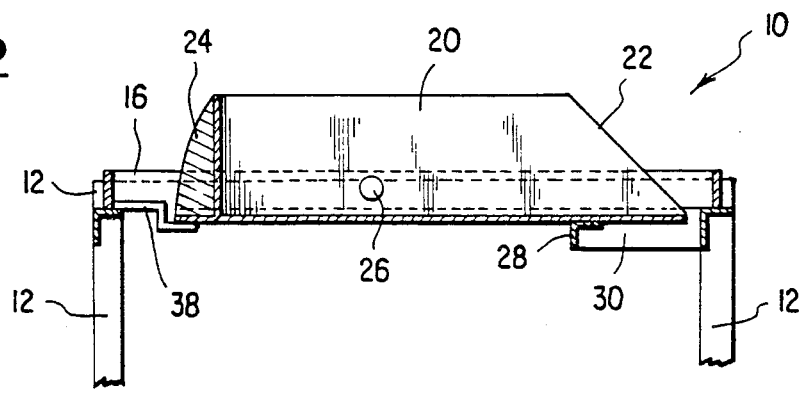
FIG. 2 is a view taken along section 2—2 of FIG. 1.
Figure 3:
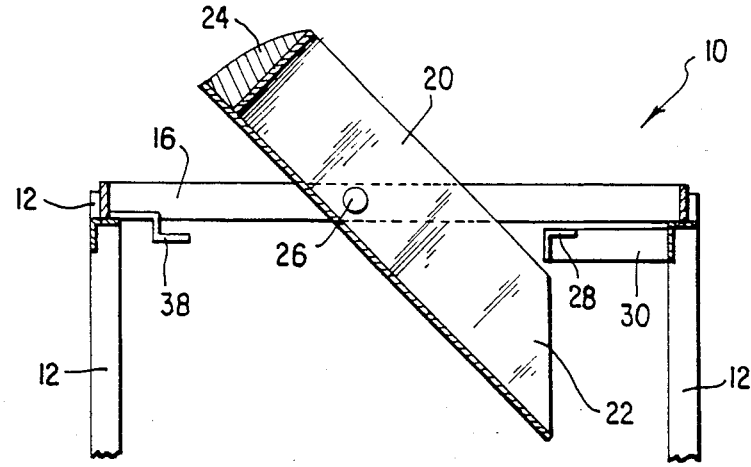
FIG. 3 is a view taken along section 3—3 of FIG. 1, showing the tray in its chip dumping position.

Referring now to FIGS. 1 to 3 of the drawings, the numeral 10 denotes a first embodiment of the wood chip sampling apparatus of this invention and includes a frame 12 fashioned from metal strip and angle iron elements, several lengths of these elements being suitably coupled together as by welding, brazing, bolts or the like. The right and left hand portions of the frame 12, as seen in FIG. 1, define rails which support a generally rectangular frame or cradle 16. A generally rectangular tray having one open side 22 and three closed sides and carrying a weight 24 at its side opposite to 22 is horizontally pivotably mounted on cradle 16 by a pair of pivot elements 26 carried by cradle 16, each pivot secured to a respective opposite sidewall of the tray. A first abutment defined by elongated metal structural elements 28 and 30 is suitably secured to frame 12 as by welding, brazing or the like and is positioned beneath tray 20 near its open side 22 in the tray chip collecting position, this being the solid line position of tray 20 as viewed in FIG. 1. First abutment 28, 30 is also seen at FIGS. 2 and 3. Cradle 16 is reciprocated back and forth in the directions indicated by the double arrow at the bottom of FIG. 1 by means of a rigid rod 32, typically of metal. The upper end of rod 32, as viewed in FIG. 1, is secured to the cradle by means of coupling 33, as by soldering, welding, or the like. A second abutment 38, in the form of a generally rectangular, bent metal bracket, is secured to one side of cradle 16 by welding, brazing or the like. Bracket 38 extends towards the interior of cradle 16 to a location beneath weight 24.

The apparatus above described is placed in the vicinity of a chip stream (not shown), such as chute A of the noted Laprise patent. The arrangement is such that when tray 20 is in the chip collecting position shown at the top of FIG. 1 and at FIG. 2, a portion of the chips from a downwardly flowing stream of wood chips falls on the tray. After a predetermined length of time, the tray is filled with the desired volume of wood chip samples, and rod 30 is then actuated so as to move tray 20 to its discharge position, this latter being a position corresponding to that of tray 21 of Laprise at his FIG. 1 over his collecting bin 2. The chip dumping tray orientation is shown at FIG. 3 and by the dashed lines at the bottom of FIG. 1 wherein the weight of the chips in the tray is such that the force of weight 24, tending to maintain the tray in contact with second abutment 38, is overcome and a sample of wood chips is then dumped into a chip bin (not illustrated), entirely similar to bin 2 of Laprise. After the chips have been dumped, tray 20 will automatically assume a horizontal position, by virtue of the weight 24 tending to rotate the tray to its horizontal position. The empty tray will be prevented from swinging (counterclockwise) to a vertical position by second abutment 38, see FIG. 2. Rod 32 is then actuated, by any suitable mechanism, back to the chip collecting position. From a consideration of FIGS. 1 and 3, it will be readily seen that first abutment 28, 30 prevents the tray from tipping in the direction indicated at FIG. 3, when filled with wood chips, until it has reached the end of abutment 28, 30 to thereby enable the tray to pivot to dump as indicated at FIG. 3. The tray of FIGS. 1 to 3 thus pivots about a horizontal axis parallel to the direction of tray reciprocation.

This back and forth or reciprocating movement of tray 20 may occur at the wish of an operator or may take place in accordance with automatic apparatus which will periodically move the tray into a stream of falling wood chips and then move the tray to the discharge or dumping position.

Figure 4:
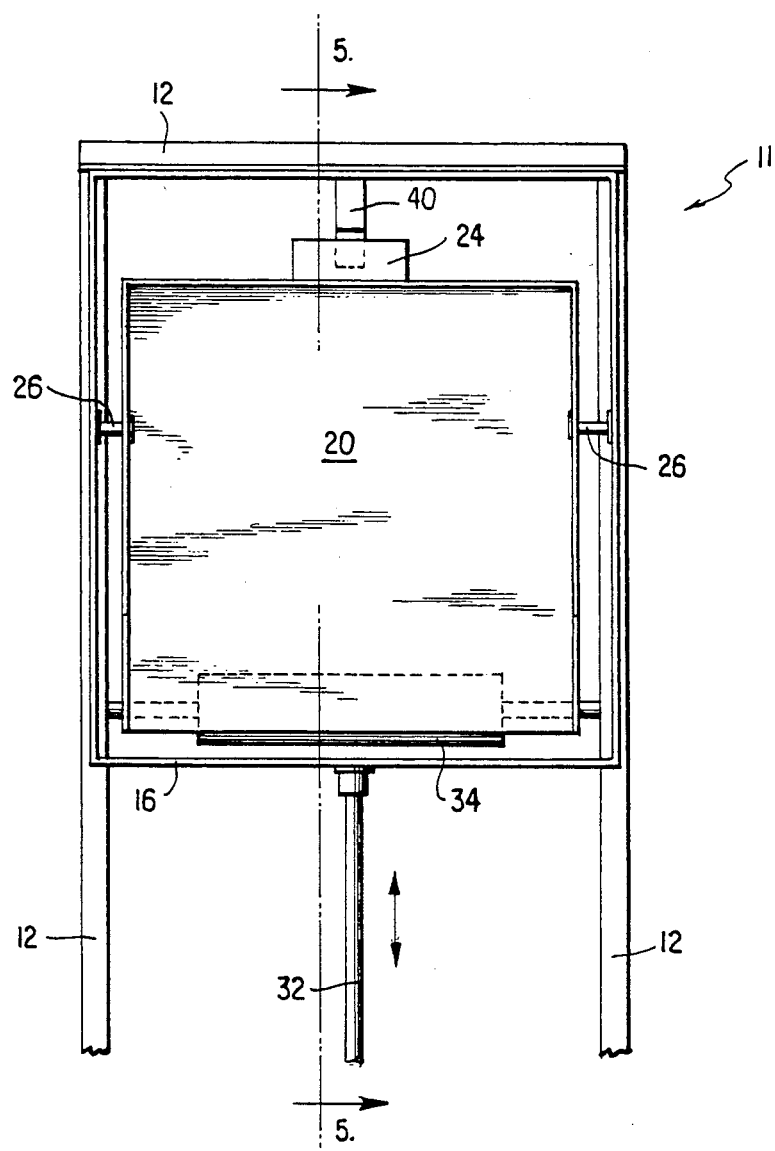
FIG. 4, is a plan view according to a second embodiment of the invention.
Figure 5:
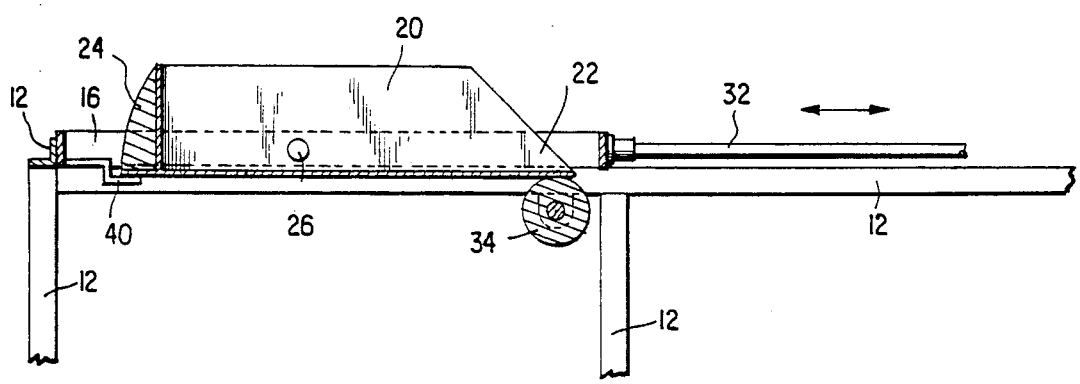
FIG. 5 is a view taken along section 5—5 of FIG. 4.
Figure 6:
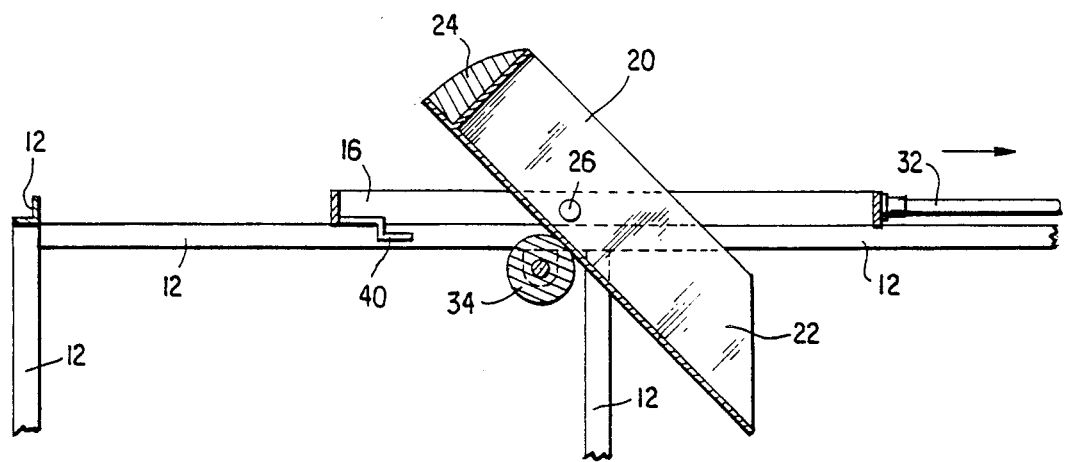
FIG. 6 is a view similar to FIG. 5 and shows the collecting tray in its chip dumping position.

Referring now to FIGS. 4 to 6 of the drawings, the numeral 11 denotes a second embodiment of the invention wherein tray 20 is pivoted about a horizontal axis which is perpendicular to the direction of the reciprocating, back and forth movement of tray 20 in passing from a chip collecting to a chip discharge location. FIGS. 4 and 5 show the chip collecting position of tray 20, the tray being of the same construction as previously described. FIG. 6 illustrates the tray in its dumping or chip discharge position.

In addition to the different orientation of the pivot axis of elements 26 of this second embodiment, the second embodiment includes a different form of the first abutment, here denoted as 34 as defined by a roller pivotable about a horizontal axis parallel to the axis defined by pivots 26. Additionally, the second abutment assumes a form indicated by the numeral 40. Abutment 40 is a metal bracket, similar to that of abutment 38, and is secured as by welding or the like to the top (as viewed in FIG. 4) side of cradle 16. It extends to a location beneath weight 24. The operation of this second embodiment is as follows. In the chip collecting position shown at FIGS. 4 and 5, the tray is placed in a stream of downwardly flowing wood chips. After the sample of wood chips is taken and the tray filled, the tray is prevented from pivoting clockwise as viewed in FIG. 5 by first abutment 34. After the tray has been moved to the right, as shown by comparison between FIGS. 5 and 6, the weight of the wood chips causes the tray to tilt as shown at FIG. 6, with the chips falling from the tray through open side 22 thereof. After full tray discharge, tray 20 will automatically assume a horizontal position due to weight 24 tending to rotate the tray in a counter-clockwise direction. It is then moved to the left by rod 32 so as to assume the position indicated at FIG. 5. Tray 20 is at all times prevented from swinging counterclockwise under the action of weight 24 by means of the second abutment 40. As with the first described embodiment, rod 32 may be automatically actuated to take samples, or samples may be taken at random.

The reader will readily visualize that the specific form of the first and second abutments may be varied. Further, the second abutment may be mounted on frame 12 instead of on cradle 16.

I claim:

1. A wood chip sampling apparatus for taking a sample of wood chips from a downwardly flowing stream of wood chips and then dumping the sample to a sample collection bin for analysis, the sampling apparatus including a horizontally reciprocating cradle, means coupled to said cradle for moving the frame reciprocatingly back and forth between a chip collecting location and a chip dumping location, supporting rails for supporting said cradle for movement in a horizontal plane, a sample collecting tray pivoted about a horizontal axis and supported within said cradle, a weight carried by said tray, the tray being open at one side to permit wood chips therein to discharge from the tray when the tray is tilted toward said open side, said weight located on that tray side opposite to said open tray side, a first abutment, said first abutment preventing the tray from tipping and dumping chips at said collecting location, the tray tilting at said dumping location when filled with collected wood chips, the; tray tilting back to a horizontal position after dumping, a second supporting abutment engaging the tray and preventing the tray from tipping when empty due to the force of said weight.

2. The apparatus of claim 1 wherein said tray pivot axis is parallel to the direction of cradle reciprocation.

3. The apparatus of claim 2 wherein said first abutment spans a portion of the distance between said collecting and said dumping locations.

4. The apparatus of claim 2 wherein said first abutment is mounted on said supporting rails.

5. The apparatus of claim 1 wherein said tray pivot axis is perpendicular to the direction of cradle reciprocation.

6. The apparatus of claim 5 wherein said first abutment is positioned near the open side of the tray in the tray chip collecting location.

7. The apparatus of claim 5 wherein said first abutment is a roller rotatable about an axis parallel to said tray pivot axis.

8. The apparatus of claim 1 wherein said second abutment is mounted on said cradle.

* * * * *